United States Patent

Mayenberger et al.

[11] Patent Number: 5,951,577
[45] Date of Patent: Sep. 14, 1999

[54] SURGICAL INSTRUMENT

[75] Inventors: Rupert Mayenberger, Rielasingen; Pedro Morales, Tuttlingen; Dieter Weisshaupt, Immendingen, all of Germany

[73] Assignee: Aesculap AG & Co. KG, Tuttlingen, Germany

[21] Appl. No.: 09/062,081

[22] Filed: Apr. 17, 1998

[30] Foreign Application Priority Data

Apr. 24, 1997 [DE] Germany ............................ 197 17 234

[51] Int. Cl.⁶ ............................ A61B 17/22; A61B 17/28
[52] U.S. Cl. ............................................ 606/159; 606/205
[58] Field of Search ................................... 606/159, 205, 606/167, 207

[56] References Cited

U.S. PATENT DOCUMENTS

| 3,038,467 | 6/1962 | Sovatkin | 600/219 |
| 4,712,545 | 12/1987 | Honkanen | 606/184 |
| 4,856,497 | 8/1989 | Westphal | 128/70 |
| 5,147,357 | 9/1992 | Rose et al. | 606/49 |
| 5,483,952 | 1/1996 | Aranyi | 600/131 |

FOREIGN PATENT DOCUMENTS

| 0 134 251 | 3/1985 | European Pat. Off. . |
| 0 513 471 | 11/1992 | European Pat. Off. . |
| 28 49 009 | 6/1979 | Germany . |
| 81 06 962 U | 9/1981 | Germany . |
| 32 23 513 | 12/1983 | Germany . |

*Primary Examiner*—Michael Buiz
*Assistant Examiner*—Vy Q. Bui
*Attorney, Agent, or Firm*—Barry R. Lipsitz; Ralph F. Hoppin

[57] ABSTRACT

In a surgical instrument, in particular, a tubular-shafted instrument, comprising two grips pivotally movable relative to one another for moving two tools movable relative to one another, and a releasable locking mechanism for securing the grips in various positions moved towards one another against movement away from one another, in order to make operation with one hand possible, it is proposed that a locking lever be pivotally mounted on one grip, the free end of the locking lever being longitudinally displaceable along a displacement path on the other grip upon pivotal movement of the grips, that a toothing be arranged along the displacement path of the free end for engagement with a toothing at the free end of the locking lever such that an opening movement of the grips is prevented, and that for release of the engagement of the two toothings the displacement path be adjustable such that the toothings disengage.

12 Claims, 4 Drawing Sheets

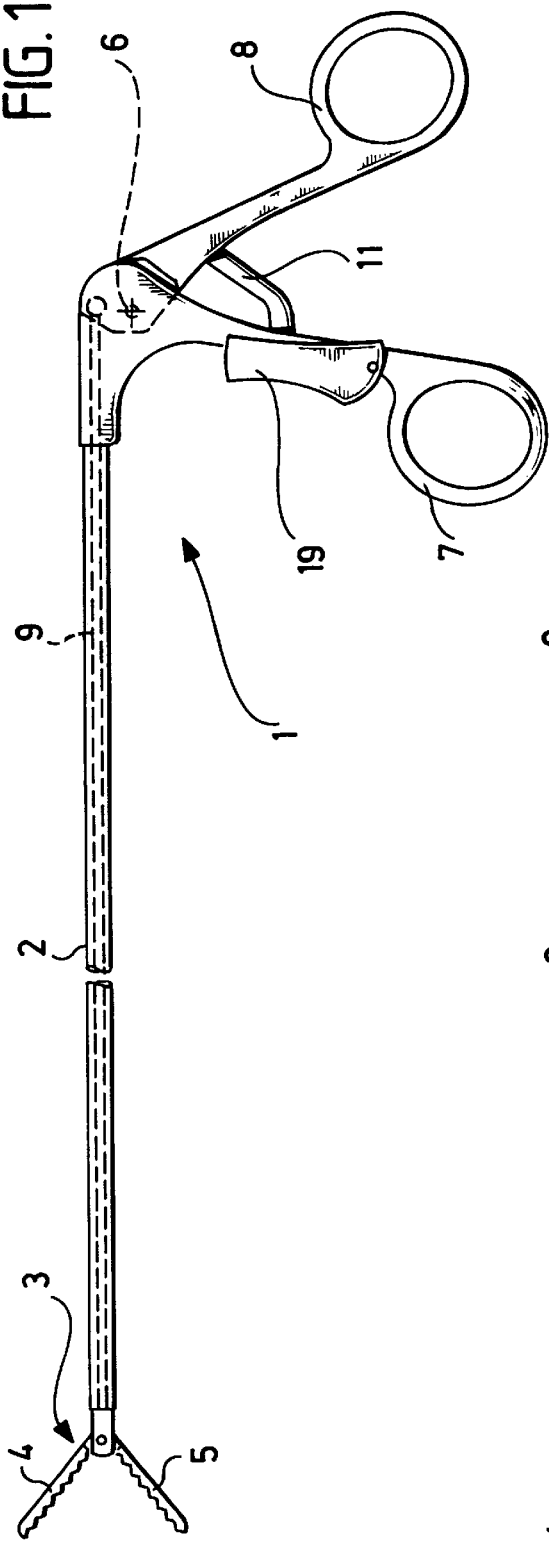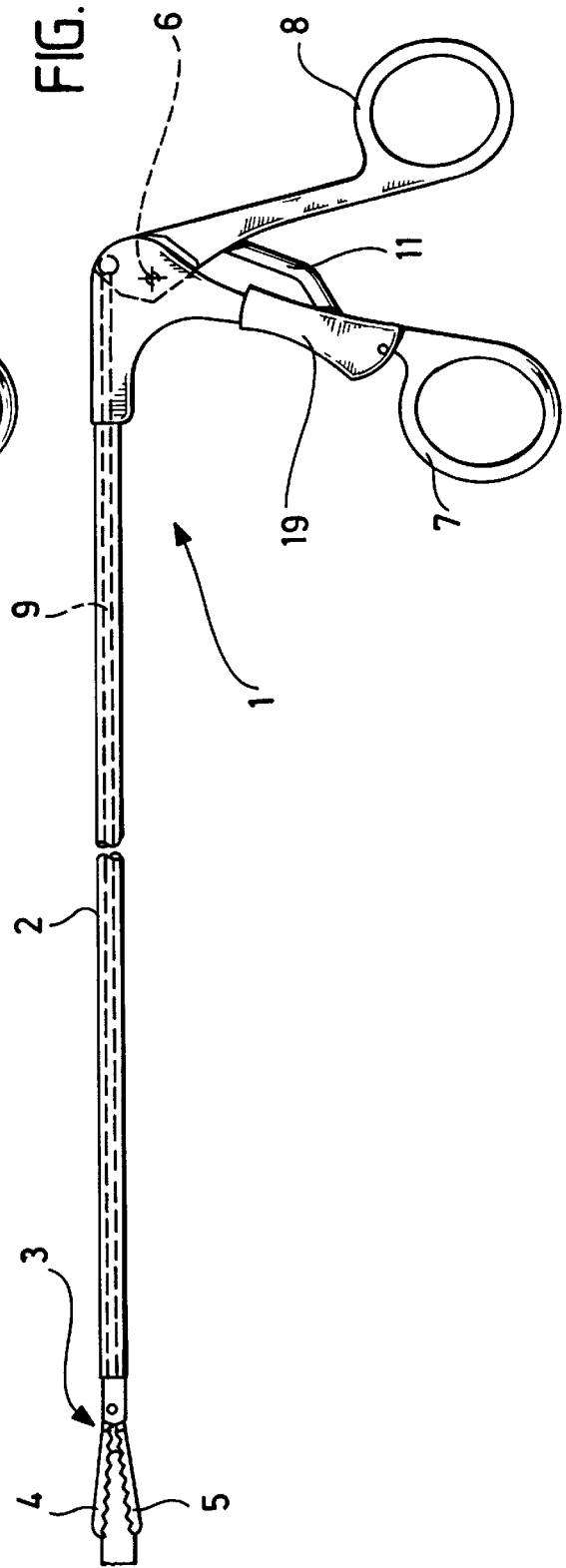

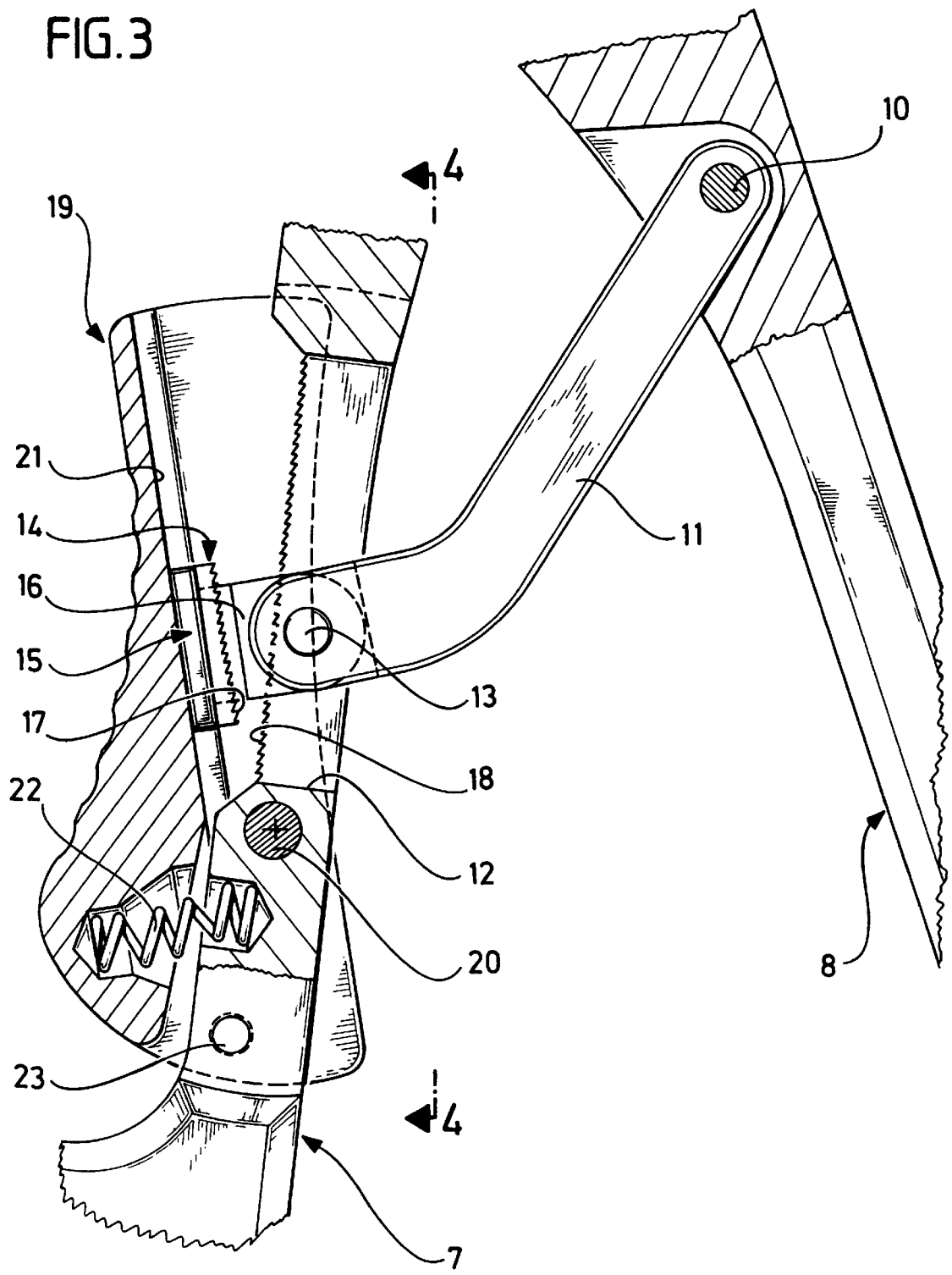

SURGICAL INSTRUMENT

BACKGROUND OF THE INVENTION

The invention relates to a surgical instrument, in particular, a tubular-shafted instrument, comprising two grips pivotally movable relative to one another for moving two tools movable relative to one another, and a releasable locking mechanism for securing the grips in various positions moved towards one another against movement away from one another.

Such an instrument is described in, for example, U.S. Pat. No. 4,712,545. The releasable locking mechanism comprises a slide on the grips which are pivotally movable relative to one another. When the grips are close together, the slide can be moved so far along the grips that opening is no longer possible. To be able to open the grips again, the closing movement must be continued, and the slide must subsequently be pushed back upwards again.

With such a construction, actuation of the instrument and the locking slide is only possible with both hands. In addition, there is the danger that the slide will become jammed.

SUMMARY OF THE INVENTION

The object of the invention is to so design a surgical instrument of the generic kind that operation with one hand is possible, and that the operator himself, on moving the grips towards one another, may choose whether he obtains automatic locking against subsequent movement apart or not.

This object is accomplished in accordance with the invention in a surgical instrument of the kind described at the outset in that a locking lever is pivotally mounted on one grip, the free end of the locking lever being longitudinally displaceable along a displacement path on the other grip upon pivotal movement of the grips, in that a toothing is arranged along the displacement path of the free end for engagement with a toothing at the free end of the locking lever such that an opening movement of the grips is prevented, and in that for release of the engagement of the two toothings, the displacement path is adjustable such that the toothings disengage.

The one grip forms together with the locking lever pivotally mounted thereon a two-armed toggle lever which stretches to different extents on closing and opening the grips. In accordance with this varying stretching, the free end of this toggle lever which is formed by the free end of the locking lever is moved along its displacement path in the other grip, and this movement can take place selectively in a completely unimpeded way by the engagement of the toothings or can be impeded by the engagement of the toothings.

It is particularly advantageous for the toothings to be of sawtooth-like design and to be oriented so as to slide on one another on moving the grips towards one another, but so as to lock on opening the grips.

In particular, the toothings can be pressed resiliently against one another.

With such a construction, the operator can choose by adjustment of the displacement path whether to have engagement of the toothings at all. In one position of the displacement path, there are no engagements and so opening and closing of the grips take place in an unimpeded and unlocked manner.

In another position of the displacement path, the toothings engage one another, and if they are of sawtooth-like design and, in particular, if they bear resiliently against one another, they can slide past one another in one direction, but not in the opposite direction. Therefore, it is possible to move the grips towards one another, but it is not possible to move the grips apart and thus open them so long as the toothings are in engagement with one another. To release the toothings, the displacement path must first be adjusted in order to thereby release the engagement of the toothings.

It is advantageous for the displacement path to be fixable in a position in which the toothings are not in engagement. Therefore, by adjusting the displacement path to this fixed position, the operator can ensure that no locking will occur, and so the grips can be freely opened and closed.

A preferred embodiment provides for the displacement path to be arranged in a guide element which is mounted for pivotal outward movement on the other grip. By pivoting this guide element it is, therefore, possible to pivot the displacement path into either the engagement position or the non-engagement position.

In particular, the guide element is pivoted by a spring into a position in which the toothings are in engagement. It is thus ensured that this spring also presses the toothings resiliently against one another.

The guide element may be fixable against the action of the spring in an outwardly pivoted position in which the toothings are disengaged.

In this case, it is expedient for a spring-loaded detent locking mechanism to be provided for fixing the guide element.

In a particularly preferred embodiment, the guide element is in the form of a grip lever on the other grip. Such a grip lever which is similar in design to the trigger of a gun can be selectively pivoted in either of the two directions by pressing on the upper or lower end. In the one direction, the grip lever is pivoted into the engagement position, in the other direction into the release position in which it is also fixable.

The locking lever may be pivotally connected at its free end to a slide means which is slidable along the displacement path and which carries one of the two toothings. The other toothing is then preferably provided on the other grip.

Further provision may be made for the locking lever to pass through an opening in the other grip and to enter into engagement on the outside thereof with the toothing of the other grip which is arranged on the outside thereof.

The following description of preferred embodiments of the invention serves in conjunction with the drawings to explain the invention in further detail.

BRIEF DESCRIPTION OF THE DRAWINGS

FIG. 1 a side view of a gripping instrument of tubular-shafted design with two pivotable and lockable grips, with the tool open;

FIG. 2 a view of the instrument of FIG. 1, with the tool closed;

FIG. 3 an enlarged view in section of the two grips of the instrument of FIGS. 1 and 2 in the area of the locking mechanism, with the locking mechanism released;

DETAILED DESCRIPTION OF THE INVENTION

Figure 4:
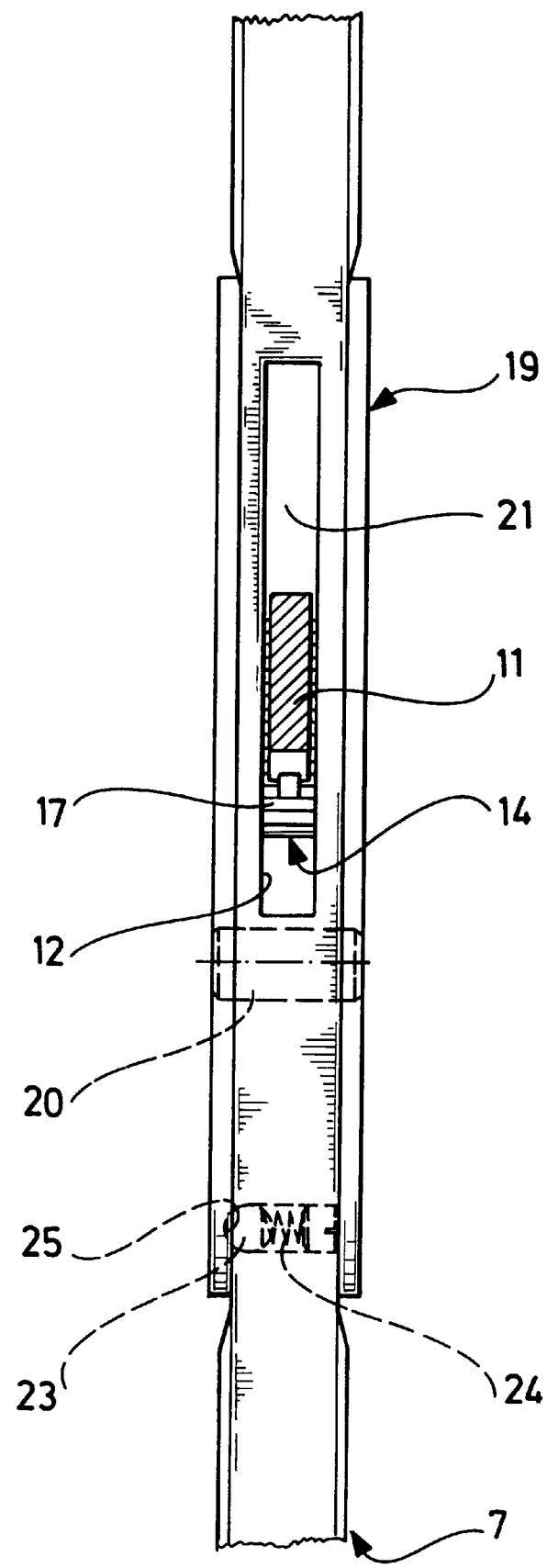
FIG. 4 a view in section taken along line 4—4 in FIG. 3.

The surgical instrument shown in the drawings is a tubular-shafted instrument 1 with a long shaft 2, at whose free end a tool 3 is arranged with two gripping jaws 4, 5 which are movable relative to each other. Arranged at the opposite end of the shaft 2 are two grips 7, 8 which are pivotable relative to each other about a transversely extending axis 6. When pivoted, the grips 7, 8 move the gripping jaws 4, 5 pivotally relative to one another via a transmitting mechanism. This transmitting mechanism can, for example, comprise, on the one hand, the shaft 2 and, on the other hand, a push-and-pull rod 9 which is longitudinally displaceable in the shaft 2, with the shaft 2 connected to the grip 7 and the push-and-pull rod 9 to the grip 8.

When the two grips 7, 8 are spaced from each other, the two gripping jaws 4, 5 are open (FIG. 1), when the grips 7, 8 are close to each other, the gripping jaws 4, 5 are closed (FIG. 2). The spaced apart position of the grips 7, 8 is, therefore, referred to in the following as opening position, the close together position as closing position.

A locking lever 11 is mounted on the one grip 8 for pivotal movement about an axis of rotation 10 extending parallel to the axis 6. The locking lever 11 dips into a slot-shaped central opening 12 on the other grip 7 and is connected there to a slide means 14 so as to be pivotable about an axis of rotation 13 extending parallel to the axis of rotation 10. This slide means 14 comprises a plate-shaped slide member 15 arranged transversely to the longitudinal direction of the locking lever 11 and a support 16 projecting vertically upwards from the center of the slide member 15. The support 16 likewise projects into the opening 12 and is articulatedly connected there to the free end of the locking lever 11. On its side facing the grip 7, the slide member 15 carries on both sides of the support 16 a toothing 17 of sawtooth cross section, and the grip 7 is provided on both sides of the central opening 12 with a matching toothing 18 extending over quite a large length. These toothings 17 and 18 are oriented such that on pressing the grip 7 and thus upon engagement of the two toothings 17, 18, the slide member 15 can be moved from the top downwards, with the toothings sliding along each other, but not from the bottom upwards. For movement from the bottom upwards it is necessary for the toothings 17 and 18 to be disengaged.

A grip lever 19 is mounted on the grip 7 for pivotal movement about an axis of rotation 20 extending parallel to the axis of rotation 13. The axis of rotation 20 is located below the central opening 12 at a distance from the lower end of the grip lever 19.

The grip lever 19 embraces the grip 7 on the front side and at the two side faces thereof and thereby covers it completely in the area of the opening 12. Arranged on the inner side of the grip lever 19 is a guideway 21 which extends essentially over the length thereof and on which the slide member 15 of the slide means 14 bears with its side facing away from the toothing 17. This guideway 21 guides the slide member 15 which is movable along this guideway 21.

Figure 5:
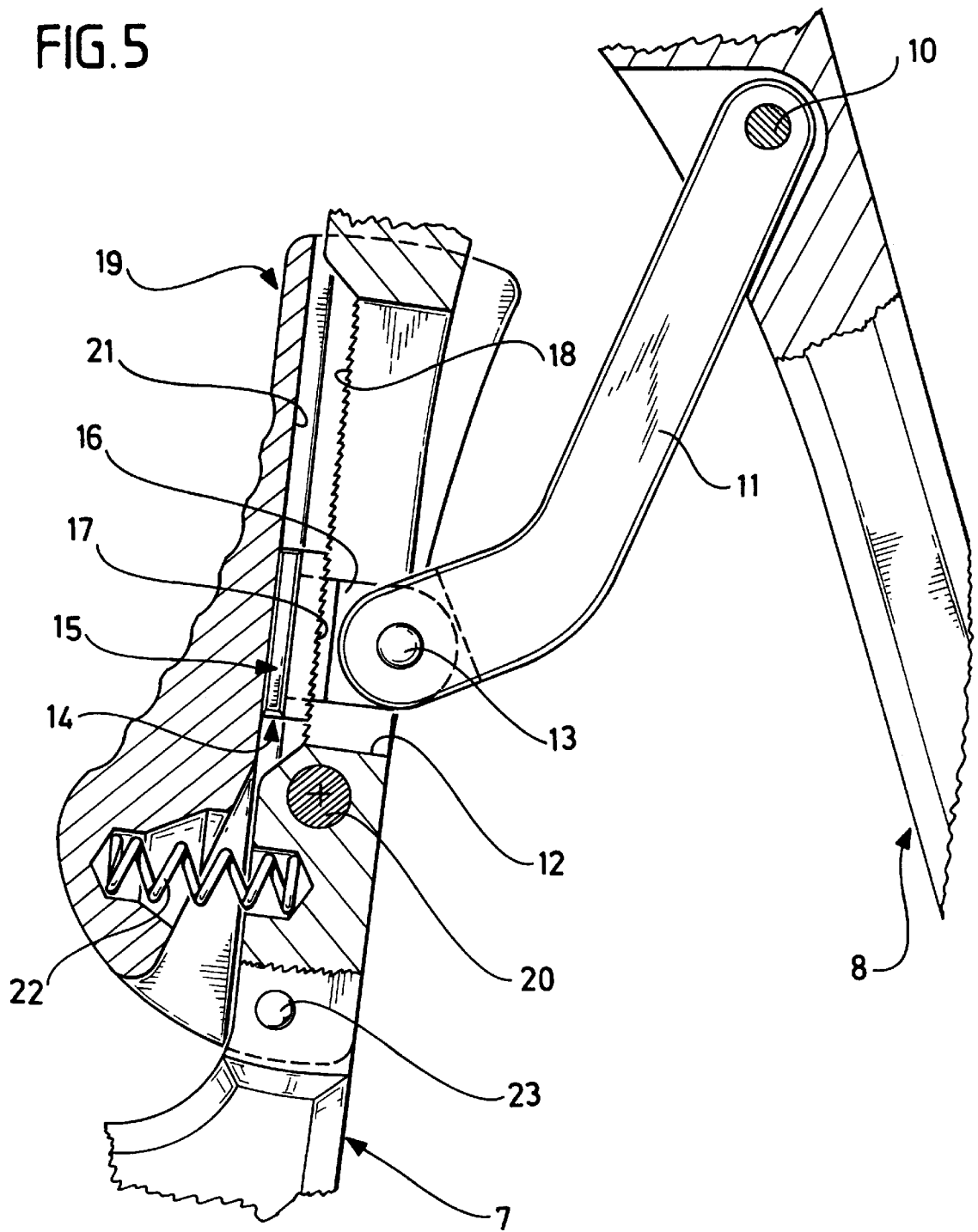
FIG. 5 a view similar to FIG. 3, with the locking mechanism effective.

By a pressure spring 22 supported, on the one hand, on the grip lever 19 and, on the other hand, on the grip 7, the grip lever 19 is pivoted into an engagement position in which the slide member 15 guided in the guideway 21 is pressed with its toothing 17 against the toothing 18 of the grip 7 (FIG. 5).

Against the action of this pressure spring 22, the grip lever 19 can be pivoted into a release position in which this engagement is released (FIG. 3), i. e., in which the toothings 17 and 18 are cannot engage one another.

The grip lever 19 can be fixed in this release position. For this purpose, there is provided in the grip 7 a pressure member 23 which protrudes at the side, for example, a ball which can be pressed against the action of a pressure spring 24 into the interior of the grip 7 and which in the pushed-out state engages a recess 25 on the inside of the grip lever 19 (FIG. 4).

When the grip lever 19 is located in the engagement position shown in FIG. 5, into which it is automatically pivoted under the action of the pressure spring 22, the toothings 18 and 17 bear against one another under spring force. When closing the grips 7, 8, the slide means 14 can, on account of the sawtooth-like design of the toothings 17 and 18, be pushed downwards thereon, with the toothing 17 sliding resiliently on the toothing 18 and after the sliding falling back into the engagement again. It is then no longer possible to open the grips 7, 8 as movement of the slide member 15 upwards is locked by the engagement of the toothings 17 and 18.

To make this opening movement possible, it is sufficient to disengage the toothings 17 and 18 by slight pressure on the lower end of the grip lever 19 until the grips 7, 8 are open.

If, on the other hand, the operator wants to deliberately dispense with such locking he can pivot the grip lever 19 by pressure on the lower end thereof against the action of the pressure spring 22 until the grip lever 19 is fully pivoted against the action of the pressure spring 22, i.e., until the resilient pressure member 23 engages the recess 25 and thereby fixes the grip lever 19 in this release position. In this release position, the toothings 17 and 18 are disengaged, i.e., the slide member 15 can move completely freely in both directions, and locking of the grips 7 and 8 does not occur.

The fixing of the grip lever 19 can be released in a simple way by pressure on the upper end of the grip lever 19. The resilient detent connection between pressure member 23 and grip lever 19 is thereby released and the grip lever 19 moves under the action of the pressure spring 22 into the engagement position shown in FIG. 5 again, in which it is possible to close, but not to open the two grips 7, 8.

Operation is possible with one hand, and this also applies to the switching of the grip lever 19 between engagement position and release position. The construction of the locking mechanism is also a very robust one, which entails few parts and guarantees safe operation.

What is claimed is:

1. A surgical instrument, comprising:
   two grips pivotally movable toward one another in a closing movement, and away from one another in an opening movement, to cause a relative movement between two tools, and
   a releasable locking mechanism movable between an engagement position and a release position,
   said releasable locking mechanism comprising:
   a locking lever pivotally mounted on one of the grips, first toothing arranged on a free end of said locking lever,
   a guide element mounted for pivotal outward movement on the other grip, and pivoted by a spring into the engagement position,
   said first toothing being longitudinally displaceable along a first direction of a displacement path on the guide element during the opening movement, and in a second, opposing direction of the displacement path during the closing movement, and
   a second toothing arranged for engagement with said first toothing at the free end of said locking lever, wherein:
   in the engagement position, the first and second toothings engage one another to prevent movement of the first toothing in the first direction so that the opening movement of said grips is prevented, while allowing the first toothing to move in the second direction so that the closing movement of the grips is allowed, and in the release position, the first and second toothings disengage one another to allow movement of the first toothing in the first direction so that the opening movement of said grips is allowed.

2. A surgical instrument as defined in claim 1, wherein:

said toothings (17, 18) are of sawtooth-like design, and are oriented so as to slide on one another when said grips are moved towards one another during the closing movement, but to lock when said grips are moved away from one another during the opening movement.

3. A surgical instrument as defined in claim 2, wherein:

said toothings (17, 18) are pressed resiliently against one another during the closing movement.

4. A surgical instrument as defined in claim 1, wherein:

said displacement path is fixable in a position in which said toothings are not in engagement.

5. A surgical instrument as defined in claim 1, wherein:

in the release position, said guide element is fixable against the action of said spring in an outwardly pivoted position in which said toothings are in disengagement.

6. A surgical instrument as defined in claim 5, further comprising:

a spring-loaded detent locking mechanism for fixing said guide element.

7. A surgical instrument as defined in claim 1, wherein:

said guide element takes the form of a grip lever on said other grip.

8. A surgical instrument as defined in claim 1, wherein:

said locking lever is pivotally connected at its free end to a slide means which is displaceable along said displacement path, and which carries one of said two toothings.

9. A surgical instrument as defined in claim 1, wherein:

said locking lever passes through an opening in said other grip and enters into engagement on the outside thereof with the toothing of said other grip, which is arranged on the outside thereof.

10. A surgical instrument as defined in claim 1, wherein:

the two grips cause the relative movement between the two tools via a shaft.

11. A surgical instrument as defined in claim 10, wherein:

the one grip is coupled to the shaft, and the other grip is coupled to a push-pull rod for causing the relative movement between the two tools.

12. A surgical instrument as defined in claim 1, wherein:

in the release position, the disengagement of the first and second toothings allows movement of the first toothing in the second direction so that the closing movement of said grips is allowed.

\* \* \* \* \*